(12) United States Patent
Ohta

(10) Patent No.: US 11,825,232 B2
(45) Date of Patent: Nov. 21, 2023

(54) RADIATION IMAGING APPARATUS AND RADIATION IMAGING APPARATUS CONTROL METHOD

(71) Applicant: CANON KABUSHIKI KAISHA, Tokyo (JP)

(72) Inventor: Koichi Ohta, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 386 days.

(21) Appl. No.: 17/327,069

(22) Filed: May 21, 2021

(65) Prior Publication Data
US 2021/0281775 A1 Sep. 9, 2021

Related U.S. Application Data

(63) Continuation of application No. PCT/JP2019/044801, filed on Nov. 15, 2019.

(30) Foreign Application Priority Data

Nov. 29, 2018 (JP) ................................ 2018-224278

(51) Int. Cl.
*H04N 5/32* (2023.01)
*A61B 6/00* (2006.01)
*G01T 1/20* (2006.01)

(52) U.S. Cl.
CPC .......... *H04N 5/3205* (2013.01); *A61B 6/482* (2013.01); *A61B 6/54* (2013.01); *G01T 1/2018* (2013.01)

(58) Field of Classification Search
CPC ........ H04N 5/3205; A61B 6/482; A61B 6/54; G01T 1/2018
See application file for complete search history.

(56) References Cited

U.S. PATENT DOCUMENTS 7,227,926 B2 * 6/2007 Kameshima ........... A61B 6/482
378/98.8
2009/0304149 A1 * 12/2009 Herrmann ................. G01T 1/17
378/62
(Continued)

FOREIGN PATENT DOCUMENTS

EP 3322177 A1 5/2018
JP 2009017476 A 1/2009
(Continued)

*Primary Examiner* — Thai Q Tran
*Assistant Examiner* — Jose M Mesa
(74) *Attorney, Agent, or Firm* — Canon U.S.A., Inc. IP Division

(57) ABSTRACT

A radiation imaging apparatus includes a pixel array including a plurality of pixels, and a readout circuit configured to read out a signal from the pixel array, each of the plurality of pixels including a conversion element configured to convert a radiation into an electrical signal, and a sample-and-hold circuit configured to perform sampling-and-holding a plurality of times on a signal from the conversion element in response to the radiation. The radiation imaging apparatus further includes a processing unit configured to perform processing of determining timings of the plurality of times of the sampling-and-holdings based on information about temporal change in radiation energy of the radiation obtained based on a signal read out by the readout circuit, and a control unit configured to perform control so that the plurality of times of sampling-and-holdings is performed by the sample-and-hold circuit at the timings determined by the processing unit.

13 Claims, 11 Drawing Sheets

(56) References Cited

U.S. PATENT DOCUMENTS

2009/0323897 A1\* 12/2009 Kameshima ......... A61B 6/4233
378/116
2015/0362601 A1    12/2015 Ofuji
2017/0269257 A1\*  9/2017 Scoullar ............... G01V 5/0041

FOREIGN PATENT DOCUMENTS

| JP | 2009504221 A | 2/2009 |
| JP | 2018075252 A | 5/2018 |
| JP | 2018129766 A | 8/2018 |
| WO | 2018/147217 A1 | 8/2018 |
| WO | 2018/198491 A1 | 11/2018 |

\* cited by examiner

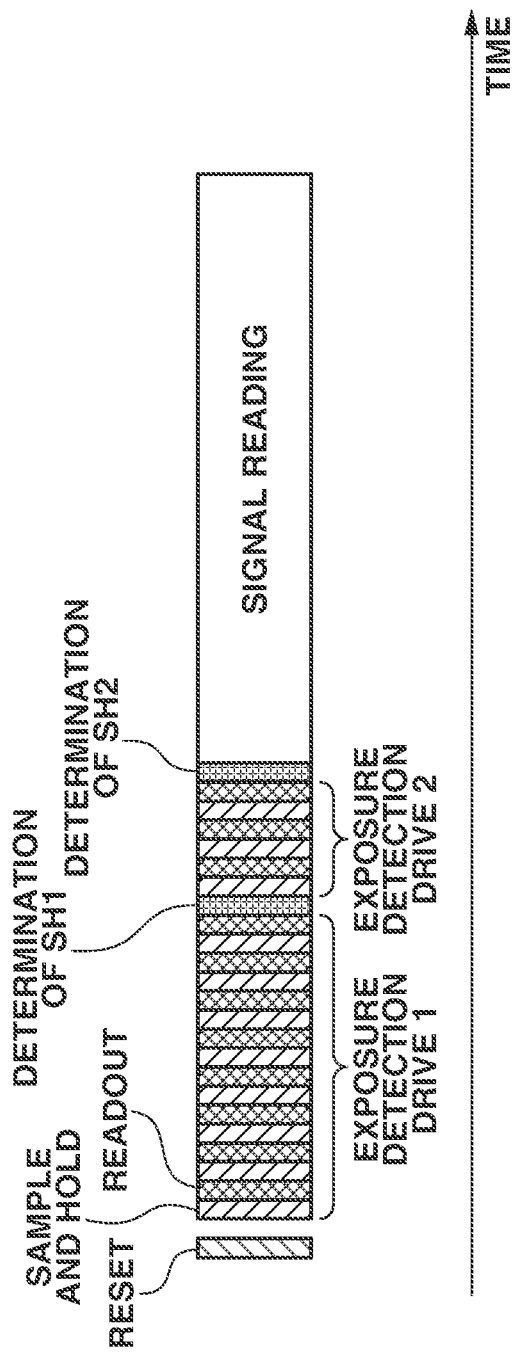

SOLID LINE: CHARGE AMOUNT
DASHED LINE: SECOND-ORDER DIFFERENTIAL VALUE OF CHARGE AMOUNT

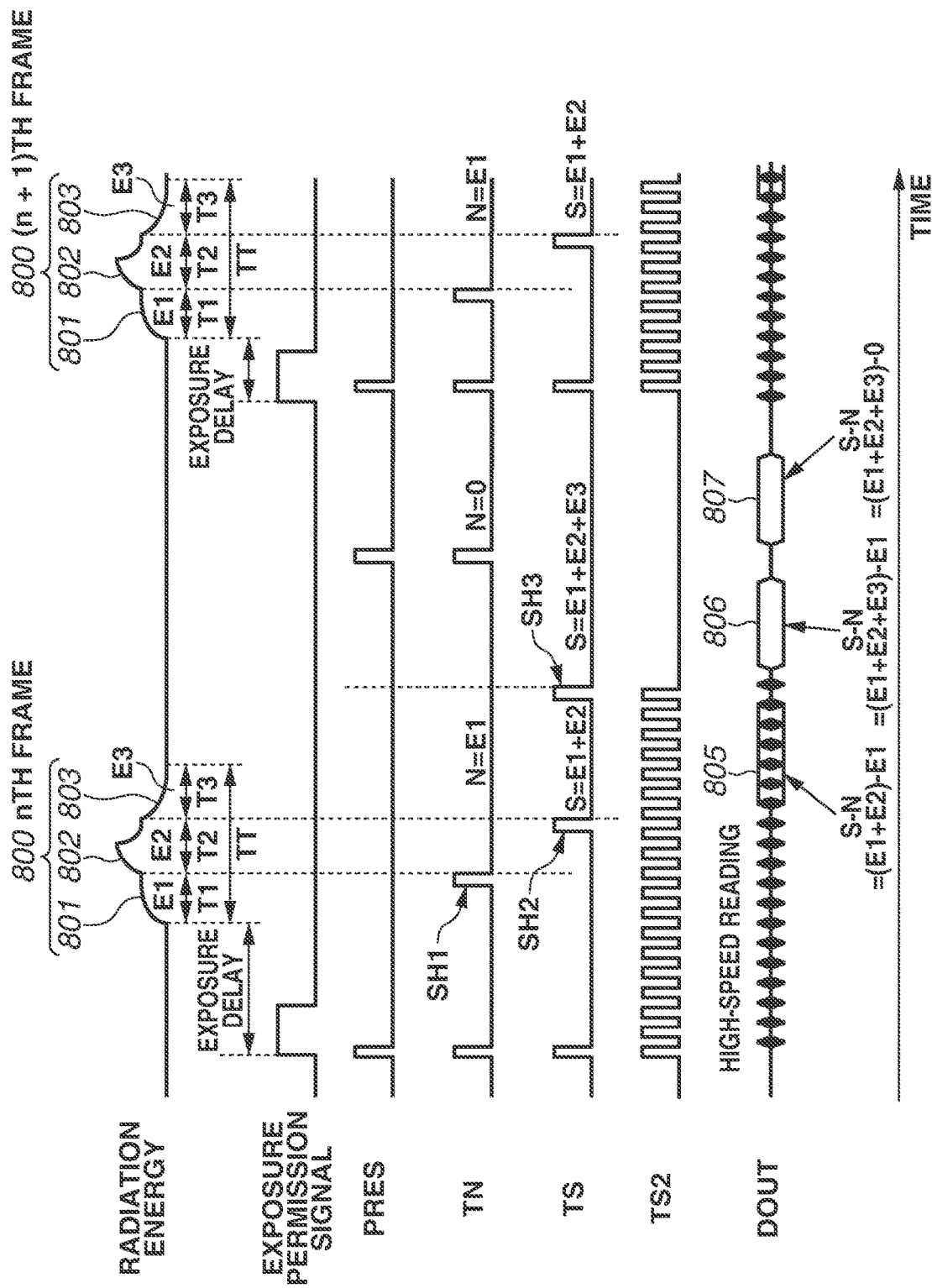

RADIATION IMAGING APPARATUS AND RADIATION IMAGING APPARATUS CONTROL METHOD

CROSS-REFERENCE TO RELATED APPLICATIONS

This application is a Continuation of International Patent Application No. PCT/JP2019/044801, filed Nov. 15, 2019, which claims the benefit of Japanese Patent Application No. 2018-224278, filed Nov. 29, 2018, both of which are hereby incorporated by reference herein in their entirety.

BACKGROUND OF THE INVENTION

Field of the Invention

The present invention relates to a radiation imaging apparatus and a radiation imaging apparatus control method.

Background Art

Imaging methods to which a radiation imaging apparatus is applied include energy subtraction method. In this energy subtraction method, image capturing is performed a plurality of times while the energy of the radiation with which an object is irradiated is changed, thus obtaining a plurality of images. The obtained images are then processed to obtain new images (for example, a bone image and a soft tissue image). Time intervals at which each of a plurality of radiation images is captured are, for example, a few seconds or more for a radiation imaging apparatus for capturing still images, 100 milliseconds or more for a radiation imaging apparatus for capturing normal videos, and 10 milliseconds or more for a radiation imaging apparatus for capturing a high-speed videos. If an object moves between these time intervals, artifacts occur due to the movement. Thus, it is difficult to obtain radiation images of objects that move quickly, such as a heart, through the energy subtraction method.

PTL 1 describes a system for performing dual energy imaging. In this system, the tube voltage of the X-ray source is first changed to a first kV value and next changed to the second kV value, in imaging. When the tube voltage is the first kV value, a first signal corresponding to a first sub-image is integrated. After this integrated signal is transferred to a sample-and-hold node, the integration is reset. Next, when the tube voltage represents the second kV value, a second signal corresponding to a second sub-image is integrated. In this way, reading of the integrated first signal and integration of the second signal are performed in parallel with each other.

In a case where a video with a plurality of frames is captured by X-ray being emitted a plurality of times through the method in PTL 1, the time from the X-ray emission to the signal transfer to the sample-and-hold node may vary between frames. This leads to a difference in energy and dose of the first sub-image between frames, and also to a difference in energy and dose of the second sub-image between frames, which may result in a drop in the accuracy of the energy subtraction.

The present invention is directed to providing a technique which is advantageous in reducing the variation in time from when the emission of radiation is started to when a signal is sampled and held.

CITATION LIST

Patent Literature

PTL 1: Japanese Unexamined Patent Application Publication No. 2009-504221

SUMMARY OF THE INVENTION

According to an aspect of the present invention, a radiation imaging apparatus includes a pixel array including a plurality of pixels, and a readout circuit configured to read out a signal from the pixel array, each of the plurality of pixels including a conversion element configured to convert a radiation into an electrical signal, and a sample-and-hold circuit configured to perform sampling-and-holding a plurality of times on a signal from the conversion element in response to the radiation. The radiation imaging apparatus further includes a processing unit configured to perform processing of determining timings of the plurality of times of the sampling-and-holdings based on information about temporal change in radiation energy of the radiation obtained based on a signal read out by the readout circuit, and a control unit configured to perform control so that the plurality of times of sampling-and-holdings is performed by the sample-and-hold circuit at the timings determined by the processing unit.

Further features of the present invention will become apparent from the following description of exemplary embodiments with reference to the attached drawings.

BRIEF DESCRIPTION OF THE DRAWINGS

FIG. 7 illustrates how a signal processing unit determines sample-and-hold timings.

FIG. 11 illustrates an operation of a radiation imaging apparatus according to the second exemplary embodiment of the present invention.

DESCRIPTION OF THE EMBODIMENTS

Hereinafter, exemplary embodiments of the present invention will be described with reference to the accompanying drawings.

Figure 1:
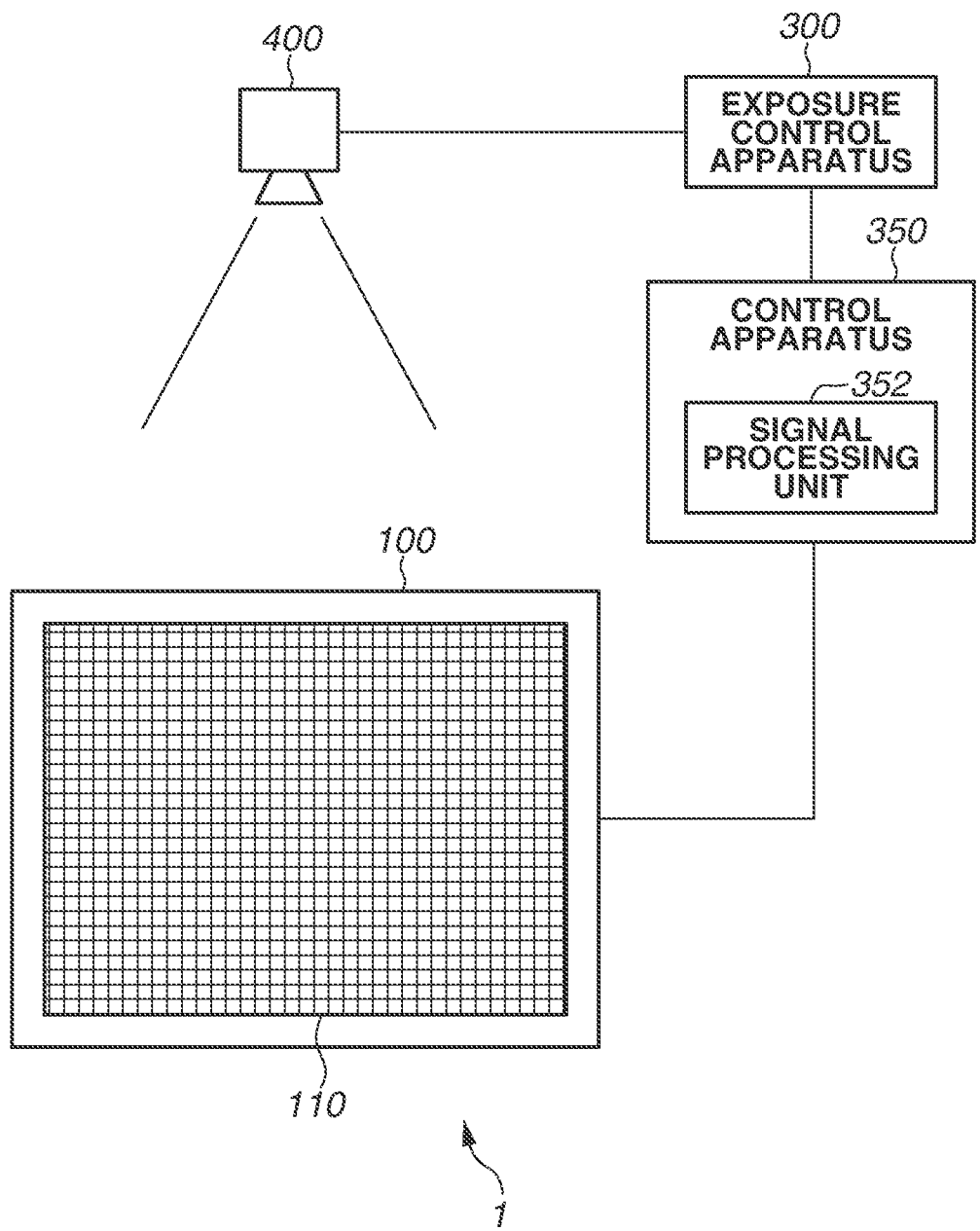
FIG. 1 illustrates a configuration of a radiation imaging apparatus according to a first exemplary embodiment of the present invention.

FIG. 1 illustrates a configuration of a radiation imaging apparatus 1 according to a first exemplary embodiment of the present invention. The radiation imaging apparatus 1 may include an imaging unit 100 including a pixel array 110 having a plurality of pixels and a signal processing unit 352 that processes signals from the imaging unit 100. The imaging unit 100 may have a shape of a panel, for example. As illustrated in FIG. 1, the signal processing unit 352 may be configured as a part of a control apparatus 350 or may be included in the enclosure of the imaging unit 100. Still alternatively, the signal processing unit 352 may be included in an enclosure different from those of the imaging unit 100 and the control apparatus 350. The radiation imaging apparatus 1 is an apparatus for obtaining radiation images through an energy subtraction method. In the energy subtraction method, the radiation imaging apparatus 1 emits radiation to an object while changing the energy of the radiation a plurality of times. The radiation imaging apparatus 1 processes a plurality of images thus captured to obtain new radiation images (for example, a bone image and a soft tissue image). The term "radiation" can include, for example, α rays, β rays, γ rays, particle rays, and cosmic rays in addition to X rays.

The radiation imaging apparatus 1 may include a radiation source 400 that emits radiation, an exposure control apparatus 300 that controls the radiation source 400, and the control apparatus 350 that controls the exposure control apparatus 300 (the radiation source 400) and the imaging unit 100. As described above, the control apparatus 350 may include the signal processing unit 352 that processes signals supplied from the imaging unit 100. The functions of the control apparatus 350 may partially or entirely be incorporated in the imaging unit 100. Alternatively, the functions of the imaging unit 100 may partially be incorporated in the control apparatus 350. The control apparatus 350 may be configured by a computer (a processor) and a memory holding a program that is provided to the computer. The signal processing unit 352 may be configured by a part of the program. Alternatively, the signal processing unit 352 may be configured by a computer (a processor) and a memory holding a program that is provided to the computer. The control apparatus 350 may partially or entirely be configured by a digital signal processor (DSP) or a programmable logic array (PLA). Each of the control apparatus 350 and the signal processing unit 352 may be designed and manufactured by a logic synthesis tool based on a file in which the operation of the corresponding one of the control apparatus 350 and the signal processing unit 352 is written.

In a case where the control apparatus 350 permits the radiation source 400 to emit radiation (exposure of radiation), the control apparatus 350 transmits an exposure permission signal to the exposure control apparatus 300. In response to receiving the exposure permission signal from the control apparatus 350, the exposure control apparatus 300 causes the radiation source 400 to emit radiation (exposure of radiation) to respond to the reception of the exposure permission signal. In a case where a video is captured, the control apparatus 350 transmits an exposure permission signal to the exposure control apparatus 300 a plurality of times. In this case, the control apparatus 350 may transmit an exposure permission signal a plurality of times to the exposure control apparatus 300 in a predetermined cycle. Alternatively, each time the imaging unit 100 becomes ready to capture the next frame, the control apparatus 350 may transmit an exposure permission signal to the exposure control apparatus 300.

The radiation source 400 may emit radiation whose energy (wavelength) changes in a continuous radiation emission period. The radiation imaging apparatus 1 uses this radiation to obtain radiation images, which are based on their respective energy levels. By processing these radiation images through the energy subtraction method, the radiation imaging apparatus 1 is able to obtain new radiation images.

Alternatively, the radiation source 400 may have a function of changing the energy (wavelength) of the radiation. The radiation source 400 may have a function of changing the energy of the radiation by changing a tube voltage (the voltage applied across positive and negative electrodes of the radiation source 400), for example.

A plurality of pixels 112 forming the pixel array 110 in the imaging unit 100 each includes a conversion element that converts the radiation into an electrical signal (for example, charges) and a reset unit that resets the conversion element. Each pixel may be configured to directly convert the radiation into an electrical signal or configured to convert the radiation into light such as visible light and then convert the light into an electrical signal. In the latter case, a scintillator may be used to convert the radiation into light. The scintillator may be shared by the plurality of pixels 112 in the pixel array 110.

Figure 2:
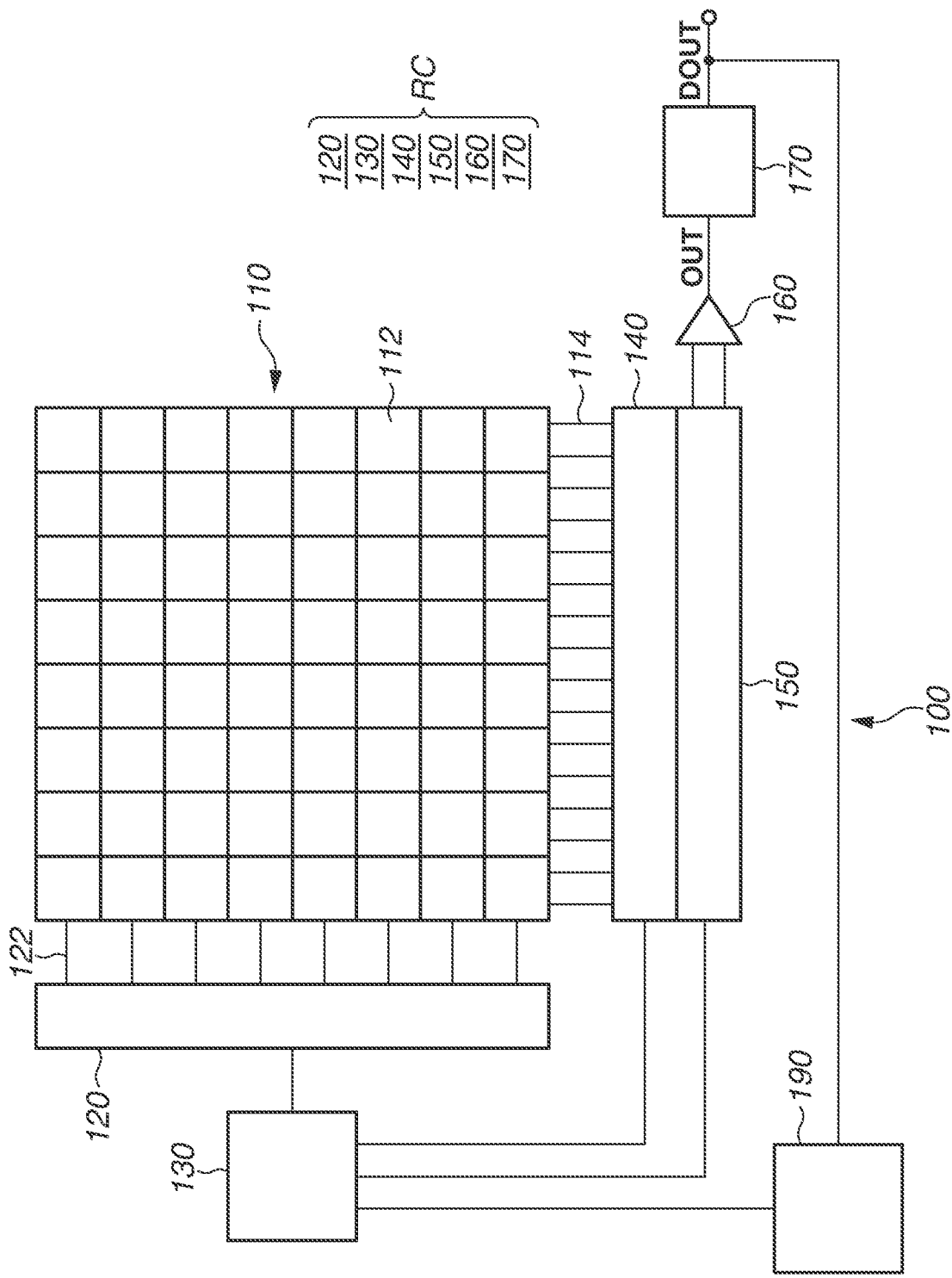
FIG. 2 illustrates a configuration example of an imaging unit.

FIG. 2 illustrates a configuration example of the imaging unit 100. The imaging unit 100 includes the pixel array 110 having the plurality of pixels 112 and a readout circuit RC for reading out signals from the plurality of pixels 112 in the pixel array 110. The plurality of pixels 112 may be arranged in a plurality of rows and in a plurality of columns. The readout circuit RC may include a row selection circuit 120, a control unit 130, a buffer circuit 140, a column selection circuit 150, an amplification unit 160, an analog-to-digital (AD) converter 170, and a detection unit 190.

The row selection circuit 120 selects a row in the pixel array 110. The row selection circuit 120 may be configured to select a row by driving a row control signal 122. The buffer circuit 140 buffers signals from the pixels 112 in the row selected by the row selection circuit 120 from among the plurality of rows in the pixel array 110. The buffer circuit 140 buffers signals which is output to a plurality of column signal transmission paths 114 in the pixel array 110. The column signal transmission path 114 in each column includes a first column signal line and a second column signal line constituting a pair of column signal lines. A noise level of a pixel 112 (in a normal mode to be described below) or a radiation signal corresponding to the radiation detected by the pixel 112 (in an extended mode to be described below) may be output to the corresponding first column signal line. The radiation signal corresponding to the radiation detected by a pixel 112 may be output to the corresponding second column signal line 322. The buffer circuit 140 may include an amplification circuit.

The column selection circuit 150 selects a signal pair in a single row buffered by the buffer circuit 140 in a predetermined order. The amplification unit 160 amplifies the signal pair selected by the column selection circuit 150. The amplification unit 160 may be configured as a differential amplifier that amplifies the difference in the signal pair (the difference between the two signals). The AD converter 170 performs analog to digital conversion on a signal OUT which is output by the amplification unit 160 into a digital signal DOUT (a radiation image signal) and outputs the digital signal DOUT.

The detection unit 190 detects the start of the emission of the radiation by the radiation source 400, based on the radiation emitted by the radiation source 400. For example, the detection unit 190 may detect the start of the radiation emission by the radiation source 400 by detecting radiation that is emitted to the pixel array 110 by the radiation source 400 based on a signal read out by the readout circuit RC from the pixel array 110. In response to detecting the start of the radiation emission by the radiation source 400, the detection unit 190 may generate a synchronization signal indicating the start of the radiation emission and supply this synchronization signal to the control unit 130.

Figure 3:
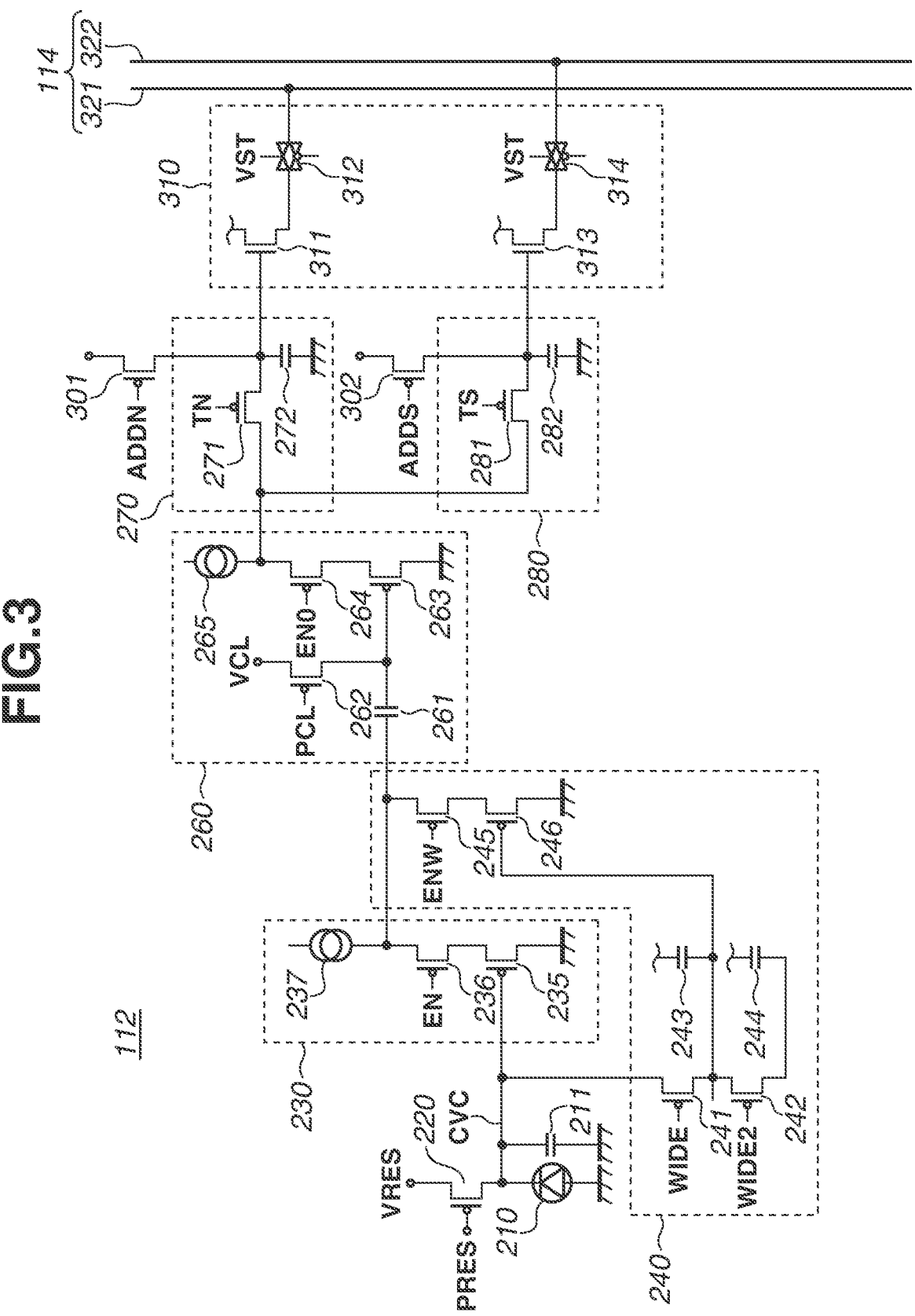
FIG. 3 illustrates a configuration example of a single pixel.

FIG. 3 illustrates a configuration example of a single pixel 112. Each pixel 112 includes, for example, a conversion element 210, a reset switch 220 (a reset unit), an amplification circuit 230, a sensitivity change unit 240, a clamp circuit 260, sample-and-hold circuits (holding units) 270 and 280, and an output circuit 310. The pixel 112 may include a normal mode and an extended mode as modes relating to an imaging method. The extended mode is a mode for obtaining radiation images through the energy subtraction method.

The conversion element 210 converts the radiation into an electrical signal. The conversion element 210 may include, for example, a scintillator that may be shared by a plurality of pixels and a photoelectric conversion element. The conversion element 210 includes a charge accumulation unit 211 that accumulates a converted electrical signal (charges), that is, an electrical signal corresponding to the radiation, and the charge accumulation unit 211 is connected to an input terminal of the amplification circuit 230.

The amplification circuit 230 may include MOS transistors 235 and 236 and a current source 237. The MOS transistor 235 is connected to the current source 237 via the MOS transistor 236. The MOS transistor 235 and the current source 237 form a source follower circuit. The MOS transistor 236 is set to on by an enable signal EN being activated. The MOS transistor 236 is an enable switch that brings the source follower circuit formed by the MOS transistor 235 and the current source 237 into an operation state.

The charge accumulation unit 211 of the conversion element 210 and the gate of the MOS transistor 235 function as a charge-to-voltage conversion unit CVC that convers charges Q accumulated by the charge accumulation unit 211 into a voltage. That is, a voltage V (=Q/C) which is defined by the charges Q accumulated by the charge accumulation unit 211 and a capacitance value C included in the charge-to-voltage conversion unit CVC appears at the charge-to-voltage conversion unit CVC. The charge-to-voltage conversion unit CVC is connected to a reset potential Vres via the reset switch 220. In response to a reset signal PRES being activated, the reset switch 220 is set to on, and the potential at the charge-to-voltage conversion unit CVC is reset to the reset potential Vres. The reset switch 220 may include a transistor including a first main electrode (a drain) connected to the charge accumulation unit 211 of the conversion element 210, a second main electrode (a source) to which the reset potential Vres is applied, and a control electrode (a gate). By an on-voltage being applied to the control electrode, this transistor brings the first main electrode and the second main electrode into conduction and resets the charge accumulation unit 211 of the conversion element 210.

The clamp circuit 260 uses a clamp capacitor 261 to clamp a reset noise level which is output from the amplification circuit 230 based on the potential of the reset charge-to-voltage conversion unit CVC. The clamp circuit 260 is a circuit for canceling the reset noise level based on the signal (the radiation signal) output from the amplification circuit 230 based on the charges (the electrical signal) converted by the conversion element 210. The reset noise level includes a kTC noise generated when the charge-to-voltage conversion unit CVC is reset. The clamp operation is performed by activating a clamp signal PCL to set a MOS transistor 262 to on, and then deactivating the clamp signal PCL to set the MOS transistor 262 to off.

The output end of the clamp capacitor 261 is connected to the gate of a MOS transistor 263. The MOS transistor 263 has a source connected to a current source 265 via a MOS transistor 264. The MOS transistor 263 and the current source 265 form a source follower circuit. The MOS transistor 264 is set to on by an enable signal EN0 supplied to the gate thereof being activated. The MOS transistor 264 is an enable switch that brings the source follower circuit formed by the MOS transistor 263 and the current source 265 into an operation state.

The output circuit 310 includes MOS transistors 311 and 313 and row selection switches 312 and 314. The MOS transistor 311 and a current source (not illustrated) connected to a column signal line 321 form a source follower circuit, and the MOS transistor 313 and a current source (not illustrated) connected to a column signal line 322 form a source follower circuit.

The radiation signal, which is the signal output from the clamp circuit 260 based on the charges generated by the conversion element 210, may be sampled and held by the sample-and-hold circuit 280. The sample-and-hold circuit 280 may include a switch 281 and a capacitor 282. The switch 281 is set to on when a sample-and-hold signal TS is activated by the row selection circuit 120. The radiation signal which is output from the clamp circuit 260 is written in the capacitor 282 via the switch 281 by the sample-and-hold signal TS being activated.

In the normal mode, when the reset switch 220 resets the potential of the charge-to-voltage conversion unit CVC and the MOS transistor 262 is set to on, the clamp circuit 260 outputs its noise level (offset component). The noise level of the clamp circuit 260 may be sampled and held by the sample-and-hold circuit 270. The sample-and-hold circuit 270 may include a switch 271 and a capacitor 272. The switch 271 is set to on by the row selection circuit 120 activating a sample-and-hold signal TN. The level of the noise which is output from the clamp circuit 260 is written in the capacitor 272 via the switch 271 by the sample-and-hold signal TN being activated. In addition, in the extended mode, the sample-and-hold circuit 270 may be used for holding the radiation signal, which is the signal output from the clamp circuit 260 based on the charges generated by the conversion element 210.

In response to a row selection signal VST being activated, signals corresponding to the signals held by the sample-and-hold circuits 270 and 280 are output to the first column signal line 321 and the second column signal line 322 forming the corresponding column signal transmission path 114. Specifically, a signal N corresponding to the signal held by the sample-and-hold circuit 270 (the noise level or the radiation signal) is output to the column signal line 321 via the MOS transistor 311 and the row selection switch 312. In addition, a signal S corresponding to the signal held by the sample-and-hold circuit 280 is output to the column signal line 322 via the MOS transistor 313 and the row selection switch 314.

The pixel 112 may include addition switches 301 and 302 for adding signals of the plurality of pixels 112. In an addition mode, addition mode signals ADDN and ADDS are activated. The activating of the addition mode signal ADDN connects the capacitors 272 of the plurality of pixels 112 to each other, and the signals (the noise levels or the radiation signals) are averaged. The activating of the addition mode signal ADDS connects the capacitors 282 of the plurality of pixels 112 to each other, and the radiation signals are averaged.

The pixel 112 may include the sensitivity change unit 240. The sensitivity change unit 240 may include switches 241 and 242, capacitors 243 and 244, and MOS transistors 245 and 246. When a first change signal WIDE is activated, the switch 241 is set to on, and the capacitance value of the first additional capacitor 243 is added to the capacitance value of the charge-to-voltage conversion unit CVC. As a result, the sensitivity of the pixel 112 is decreased. When a second change signal WIDE2 is also activated, the switch 242 is also set to on, and the capacitance value of the second additional capacitor 244 is added to the capacitance value of the charge-to-voltage conversion unit CVC. As a result, the sensitivity of the pixel 112 is further decreased. By adding this function of decreasing the sensitivity of the pixel 112, the dynamic range can be widened. In a case where the first change signal WIDE is activated, an enable signal ENW may be activated. In such a case, the MOS transistor 246 performs a source follower operation. When the switch 241 in the sensitivity change unit 240 is set to on, the potential of the charge accumulation unit 211 of the conversion element 210 may be changed by charge redistribution. As a result, a part of the signal may be destroyed.

The reset signal Pres, the enable signal EN, the clamp signal PCL, the enable signal ENO, the sample-and-hold signals TN and TS, and the row selection signal VST are control signals that is controlled (driven) by the row selection circuit 120 and correspond to the corresponding row control signal 122 in FIG. 2. In addition, the row selection circuit 120 generates the reset signal Pres, the enable signal EN, the clamp signal PCL, the enable signal ENO, the sample-and-hold signals TN and TS, and the row selection signal VST in accordance with a timing signal supplied from the control unit 130.

For the pixel 112 configured as illustrated in FIG. 3, signal destruction does not occur at, for example, the charge accumulation unit 211 of the conversion element 210 when the sampling-and-holding is performed. That is, with the pixel 112 configured as illustrated in FIG. 3, the radiation signal can be read out non-destructively. This configuration as described above is advantageous in radiation imaging to which the following energy subtraction method is applied.

Hereinafter, the extended mode for obtaining radiation images through the energy subtraction method will be described. The extended mode may include the following four sub-modes (extended modes 1 to 4). Herein, the extended mode 1 is a comparative example, and the extended modes 2 to 4 are improvement examples of the comparative example 1.

Figure 4:
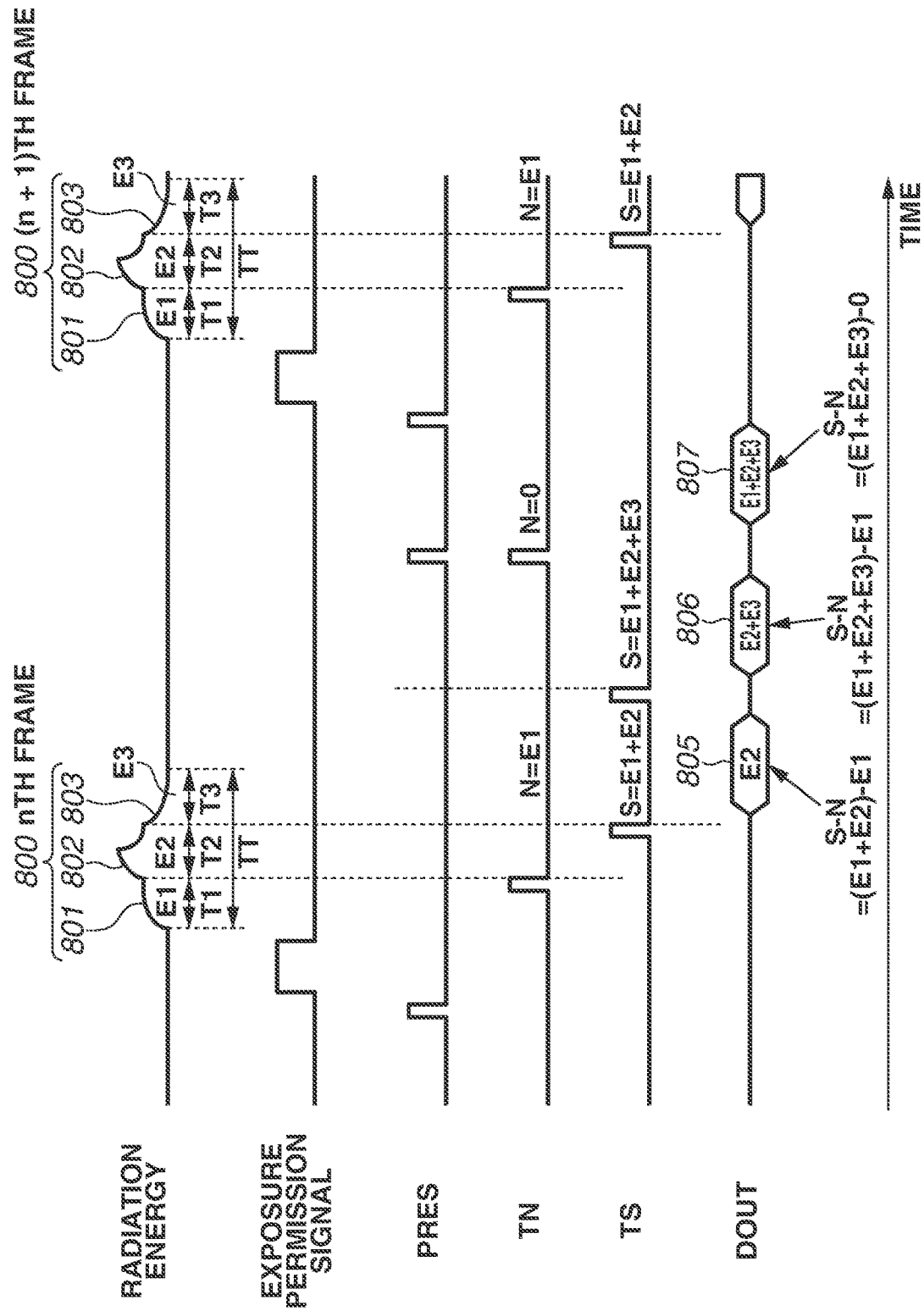
FIG. 4 illustrates an operation of the radiation imaging apparatus in an extended mode 1 (a comparative example).

FIG. 4 illustrates an operation of the radiation imaging apparatus 1 in the extended mode 1 (the comparative example). In FIG. 4, the horizontal axis represents time, and "radiation energy" represents the energy of the radiation emitted from the radiation source 400 to the imaging unit 100. In addition, "PRES" represents the reset signal RPES, and "TS" represents the sample-and-hold signal TS. In addition, "DOUT" represents the output of the AD converter 170. The synchronization of the emission of the radiation from the radiation source 400 and the operation of the imaging unit 100 may be controlled by the control apparatus 350, which generates an exposure permission signal. The operation control of the imaging unit 100 is performed by the control unit 130. In a period in which the reset signal PRES is activated, the clamp signal PCL is also activated in a predetermined period, and the noise level is clamped by the clamp circuit 260.

As illustrated in FIG. 4, the energy (wavelength) of the radiation 800 emitted from the radiation source 400 changes in a radiation emission period. This change can result from the control of the tube voltage of the radiation source 400 in two levels, which are low and high energy levels, and each of the tube voltages being slow at a rising edge and a falling edge. Thus, the following description assumes that the radiation 800 includes a radiation 801 in a low energy emission period, a radiation 802 in a high energy emission period, and a radiation 803 in a low energy radiation falling period. The radiations 801 to 803 have energies E1 to E3, respectively, which are different from each other. By using this feature, radiation images can be obtained through the energy subtraction method.

The control unit 130 defines a first period T1, a second period T2, and a third period T3 so that the first period T1, the second period T2, and the third period T3 correspond to the low energy emission period, the high energy emission period, and the low energy radiation falling period, respectively, as described below. Each pixel 112 outputs a first signal corresponding to the electrical signal generated by the conversion element 210 in the first period T1. In addition, each pixel 112 outputs a second signal corresponding to the electrical signals generated by the conversion element 210 in the first period T1 and the second period T2. In addition, each pixel 112 outputs a third signal corresponding to the electrical signals generated by the conversion element 210 in the first period T1, the second period T2, and the third period T3. The first period T1, the second period T2, and the third period T3 are periods different from each other. The radiation having the first energy E1 is t emitted in the first period T1. The radiation having the second energy E2 is emitted in the second period T2. The radiation having the third energy E3 is emitted in the third period T3.

In the extended mode 1, in an emission period TT in which the radiation 800 is emitted, the conversion element 210 of the individual pixel 112 is not reset (the reset signal PRES is not activated). Thus, in the emission period TT in which the radiation 800 is emitted, the electrical signal (charges) corresponding to the incident radiation is continuously accumulated in the conversion element 210. It is advantageous to not reset the conversion element 210 of the pixel 112 in the emission period TT, in which the radiation 800 is emitted, for obtaining radiation images for the energy subtraction method in a shorter time while the emission of the radiation that does not contribute to imaging is reduced.

Before the emission of the radiation 800 (to the imaging unit 100), the reset signal PRES is activated across a predetermined period, and the conversion element 210 is consequently reset. In this operation, the clamp signal PCL is also activated across a predetermined period, and the reset level (noise level) is clamped by the clamp circuit 260.

After the reset signal PRES is activated across the predetermined period, an exposure permission signal is transmitted from the exposure control apparatus 300 to the radiation source 400, and, in response to this exposure permission signal, the radiation is emitted from the radiation source 400. After a predetermined period elapses from the activation of the reset signal PRES across the predetermined period, the sample-and-hold signal TN is activated across a predetermined period. As a result, a signal (E1) corresponding to the electrical signal generated by the conversion element 210 of the pixel 112 in the pixel array 110 upon reception of the emission of the radiation 801 having the energy E1 is sampled and held by the sample-and-hold circuit 270.

After a predetermined period has elapsed from the activation of the sample-and-hold signal TN across the predetermined period, the sample-and-hold signal TS is activated across a predetermined period. This causes the sample-and-hold circuit 280 to sample and hold a signal (E1+E2) corresponding to the electrical signal generated by the conversion element 210 of the pixel 112 in the pixel array 110 upon reception of the emission of the radiation 801 having the energy E1 and the radiation 802 having the energy E2.

Next, a signal corresponding to the difference between the signal (E1) sampled and held by the sample-and-hold circuit 270 and the signal (E1+E2) sampled and held by the sample-and-hold circuit 280 is output as a first signal 805 from the readout circuit RC ("readout"). In FIG. 4, "N" represents the signal that is sampled and held by the sample-and-hold circuit 270 and is output to the first column signal line 321, and "S" represents the signal that is sampled and held by the sample-and-hold circuit 280 and is output to the second column signal line 322.

Next, after a predetermined period has elapsed from the activation of the sample-and-hold signal TS across the predetermined period (after the emission of the radiation 803 having the energy E3 (the emission of the radiation 800)), the sample-and-hold signal TS is activated again across a predetermined period. This causes the sample-and-hold circuit 280 to sample and hold a signal (E1+E2+E3) corresponding to the electrical signal generated by the conversion element 210 of the pixel 112 in the pixel array 110 upon reception of the emission of the radiations 801 to 803 having the energies E1 to E3, respectively.

Next, a signal corresponding to the difference between the signal (E1) sampled and held by the sample-and-hold circuit 270 and the signal (E1+E2+E3) sampled and held by the sample-and-hold circuit 280 is output as a second signal 806 from the readout circuit RC.

The reset signal PRES is then activated across a predetermined period, and the sample-and-hold signal TN is activated across a predetermined period. As a result, a reset level (0) is sampled and held by the sample-and-hold circuit 270. A signal corresponding to the difference between the signal (0) sampled and held by the sample-and-hold circuit 270 and the signal (E1+E2+E3) sampled and held by the sample-and-hold circuit 280 is then output as a third signal 807 from the readout circuit RC.

By repeating the operation as described above a plurality of times, radiation images with a plurality of frames (that is, a video) can be obtained.

The signal processing unit 352 can obtain the first signal 805 (E2), the second signal 806 (E2+E3), and the third signal 807 (E1+E2+E3) as described above. The signal processing unit 352 can obtain an emission amount e1 of the radiation 801 having the energy E1, an emission amount e2 of the radiation 802 having the energy E2, and an emission amount e3 of the radiation 803 having the energy E3 based on the first signal 805, the second signal 806, and the third signal 807. More specifically, the signal processing unit 352 can obtain the emission amount e3 of the radiation 803 having the energy E3 by calculating the difference ((E2+E3)−E2) between the first signal 805 (E2) and the second signal (E2+E3). In addition, the signal processing unit 352 can obtain the emission amount e1 of the radiation 801 having the energy E1 by calculating the difference ((E1+E2+E3)−(E2+E3)) between the second signal 806 (E2+E3) and the third signal 807 (E1+E2+E3). In addition, the first signal 805 (E2) represents the emission amount e2 of the radiation 802 having the energy E2.

Thus, the signal processing unit 352 can obtain a radiation image through the energy subtraction method, based on the emission amount e1 of the radiation 801 having the energy E1, the emission amount e2 of the radiation 802 having the energy E2, and the emission amount e3 of the radiation 803 having the energy E3. A method selected from various methods can be adopted as the energy subtraction method. For example, a bone image and a soft tissue image can be obtained by calculating the difference between a radiation image having a first energy and a radiation image having a second energy. Alternatively, a bone image and a soft tissue image may be generated by solving a non-linear simultaneous equation based on a radiation image having the first energy and a radiation image having the second energy. In addition, a contrast image and a soft tissue image can also be obtained based on a radiation image having the first energy and a radiation image having the second energy. An electron density image and an effective atomic number image can also be obtained based on a radiation image having the first energy and a radiation image having the second energy.

Figure 5:
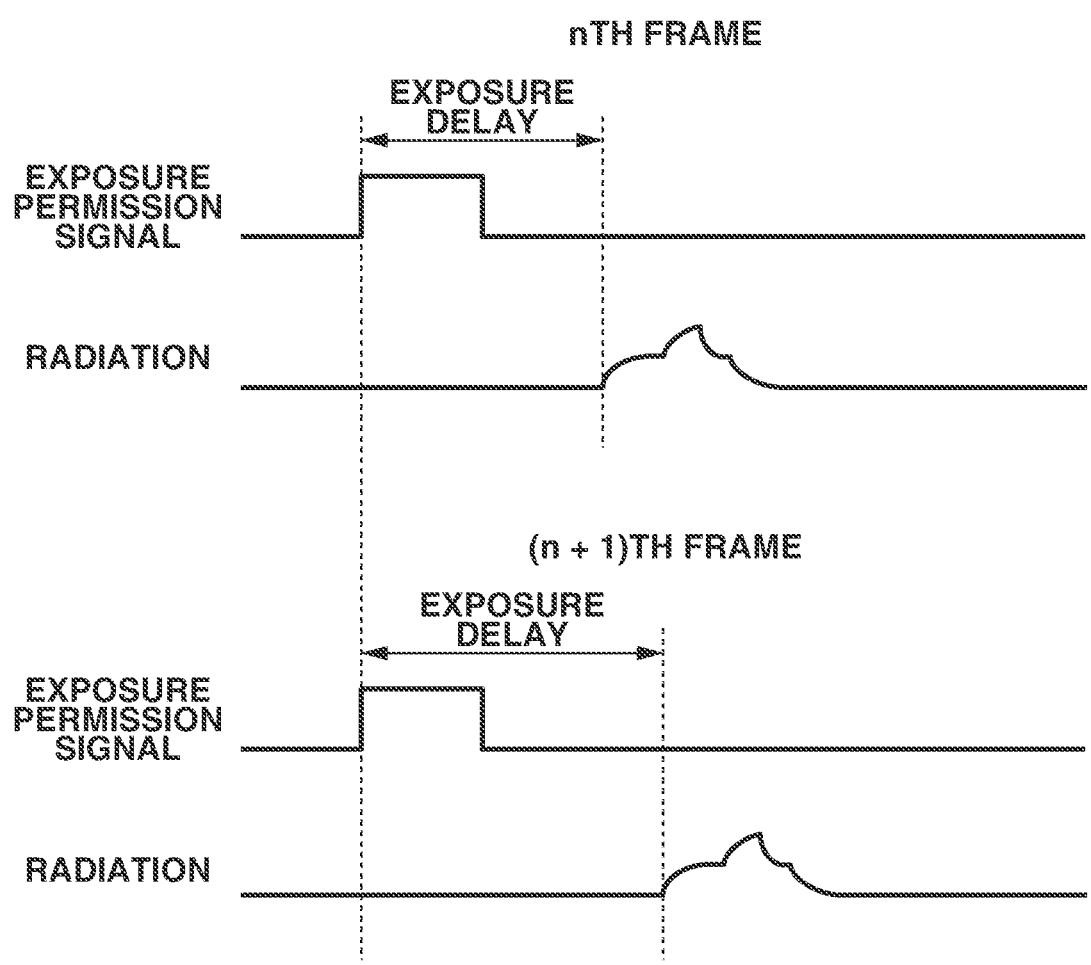
FIG. 5 illustrates a problem in the extended mode 1 (the comparative example).

A problem with the extended mode 1 (the comparative example) will be described with reference to FIG. 5. As illustrated in FIG. 5, the time (referred to as "exposure delay") between when the control apparatus 350 transmits an exposure permission signal to the exposure control apparatus 300 and when the radiation source 400 starts emitting the radiation (exposure of the radiation) could differ depending on the frame. In the example in FIG. 5, the exposure delay in the (n+1)th frame is larger than the exposure delay in the nth frame.

That the exposure delay differs between frames refers to, if it is explained with reference to FIG. 4, that the periods T1 and T2, from when the radiation 800 starts emitting the radiation to when the sample-and-hold circuits 270 and 280, respectively, completes the sampling-and-holding. Thus, the radiation energies and the emission amounts (doses) detected as the first signal 805, the second signal 806, and the third signal 807 could vary between frames. This means that the radiation energies and the emission amounts (doses) detected as the emission amount e1, the emission amount e2, and the emission amount e3 could vary between frames, and that the accuracy of the energy subtraction based on the emission amount e1, the emission amount e2, and the emission amount e3 could be decreased. Thus, artifacts and/or blinking could occur in the resultant video.

Figure 6:
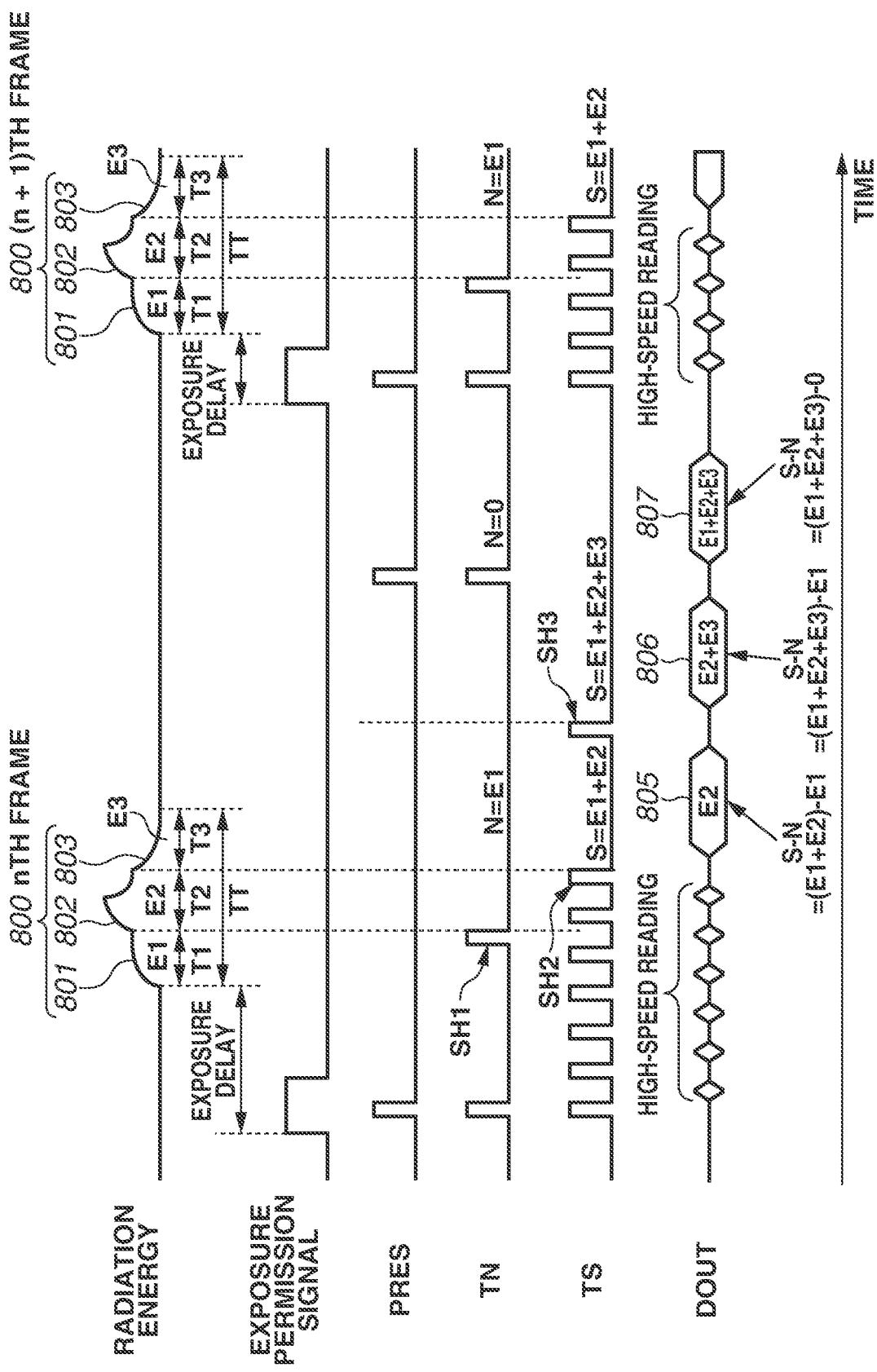
FIG. 6 illustrates an operation of the radiation imaging apparatus in an extended mode 2.

FIG. 6 illustrates an operation of the radiation imaging apparatus 1 in the extended mode 2. What is not described as the extended mode 2 may be the same as those in the extended mode 1. To solve the issue in the extended mode 1 (the comparative example), it is necessary to cause the sample-and-hold circuits 270 and 280 in the pixel 112 to perform the sampling-and-holding in synchronization with the radiation actually emitted from the radiation source 400, not with an exposure permission signal. Thus, in response to the control unit 130 receiving an exposure permission signal, the readout circuit RC non-destructively reads out the signal from at least one of the sample-and-hold circuits 270 and 280 a plurality of times. Based on the signals read out by the readout circuit RC the plurality of times, information about the temporal change in (waveform of) the radiation energy emitted from the radiation source 400 can be acquired. In addition, based on the signals read out the plurality of times, the timings of a plurality of samplingand-holdings SH1, SH2, and SH3 in each of the plurality of pixels 112 in the pixel array 110 are determined. That is, based on the acquired information about the temporal change in the radiation energy, the timings of the plurality of sampling-and-holdings SH1, SH2, and SH3 in each of the plurality of pixels 112 in the pixel array 110 can be determined. Preferably, the readout circuit RC performs the sampling-and-holding a plurality of times by using at least one of the sample-and-hold circuits 270 and 280 and non-destructively reads out the signals sampled and held by at least one of the sample-and-hold circuits 270 and 280 a plurality of times. Next, the signal processing unit 352 determines the timings of the plurality of sampling-and-holdings SH1, SH2, and SH3 in each of the plurality of pixels 112 in the pixel array 110 based on the temporal change amounts (differential values) of the signals read out the plurality of times. That is, the timings of the plurality of sampling-and-holdings SH1, SH2, and SH3 in each of the plurality of pixels 112 in the pixel array 110 can be determined by using the temporal change amounts (differential values) of the signals which serve as the information about the temporal change in (waveform of) the radiation energy. In the period between the first sampling-and-holding SH1 and the last sampling-and-holding SH3 among the plurality of sampling-and-holdings SH1, SH2, and SH3, the reset switch 220 does not reset the conversion element 210.

Here, to obtain a radiation image through the energy subtraction method, at least one of the timings of the plurality of sampling-and-holdings SH1, SH2, and SH3 is within a radiation emission period TT. In the first exemplary embodiment, among the timings of the three sampling-and-holdings SH1, SH2, and SH3, the timings of the two sampling-and-holdings SH1 and SH2 are within a radiation emission period TT. Each of the timings of the plurality of sampling-and-holdings SH1 and SH2 is determined in accordance with the temporal change amounts of the signals read out by the signal processing unit 352 the plurality of times. That is, in a frame, the sampling-and-holding SH1 is performed at timing t1 at which the low energy radiation 801 changes to the high energy radiation 802, and the sampling-and-holding SH2 is performed at timing t2 at which the high energy radiation 802 changes to the radiation 803. Here, if the waveform of the radiation emitted from the radiation source 400 is constant, the period from the sampling-and-holding SH1 to the end of the sampling-and-holding SH2 is made to be constant. The timing of the sampling-and-holding SH3 can be uniquely determined at a timing at which the readout after SH2 is in time for the next frame. In addition, the timing at which the reset level (0) is sampled and held by the sample-and-hold circuit 270 may uniquely be determined after the readout of the third signal 807 after SH2. In this way, reduction of the accuracy of the energy subtraction is prevented, thus reducing the artifacts and/or blinking in the video.

FIG. 7 illustrates an example of a method in which the signal processing unit 352 determines the sample-and-hold timings from the signals sampled and held by the sample-and-hold circuit 280. The activation of the reset signal PRES sets the reset switch 220 to on, the charge accumulation unit 211 of the conversion element 210 is "reset", and after that exposure detection drive is performed. In response to the start of the emission of the radiation being detected in this exposure detection drive, the exposure detection drive is shifted to energy subtraction drive. In reset RD, in response to receiving an exposure permission signal, the reset signal PRES is activated across a predetermined period, which resets the conversion element 210. At this time, the clamp signal PCL is also activated across the predetermined period, and the reset level (noise level) is clamped by the clamp circuit 260. In addition, in this period, since the sample-and-hold signal TN and the sample-and-hold signal TS are also activated across the predetermined period, the capacitor 272 of the sample-and-hold circuit 270 and the capacitor 282 of the sample-and-hold circuit 280 are set to a reset level. As a result, the sample-and-hold circuit 270 and the sample-and-hold circuit 280 are reset. In the reset RD, if the first change signal WIDE and the second change signal WIDE2 of the sensitivity change unit 240 are activated across the predetermined period, the first additional capacitor 243 and the second additional capacitor 244 are also reset. Thus, it is desirable that the additional capacitors be reset as needed. As described above, in the reset RD, along with the conversion element 210 being reset, the kTC noise of the clamp circuit 260 and the noise component resulting from the offset of a first amplification transistor are held by the clamp capacitor 261, and the capacitors 272 and 282 are initialized. In particular, since the capacitor 272 of the sample-and-hold circuit 270 and the capacitor 282 of the sample-and-hold circuit 280 are set to a reset level by the reset RD, it is possible to accurately detect minute signal change in the exposure detection drive. After the reset RD, the exposure detection drive is performed. That is, the reset RD is performed before the start of the emission of the radiation is detected. The exposure detection drive includes a repetition of "sample-and-hold" by the sample-and-hold circuits 270 and 280 in the individual pixel 112 and "readout" of the signal from the individual pixel 112 by the readout circuit RC. The exposure detection drive and the energy subtraction drive are controlled by the control unit 130. If the signal read out from the pixel 112 by the readout circuit RC exceeds a threshold, the detection unit 190 may determine that the emission of the radiation by the radiation source 400 is started and generate a synchronization signal. In response to this, the control unit 130 may start the energy subtraction drive. However, in accordance with the method illustrated in FIG. 7, even if control in response to the generation of a synchronization signal is not performed, the energy subtraction drive can be controlled. The energy subtraction drive includes the plurality of sampling-and-holdings SH1, SH2, and SH3, which are performed by the sample-and-hold circuits 270 and 280 of the plurality of pixels 112, and the readout operation by the readout circuit RC. The readout operation by the readout circuit RC includes outputting the first signal 805, the second signal 806, and the third signal 807.

It is preferable that the repetition of "sample-and-hold" and "readout" in the exposure detection drive be performed more quickly than in the repetition of "sample-and-hold" and "readout" in acquiring a radiation image (for example, on the order of microseconds (μs)). This is because the timing at which the detection of the start of the radiation emission is delayed by the time needed for the "sample-and-hold" and "readout". For a faster operation, the binning (the number of pixels added) in the readout may be changed in the exposure detection drive period. As the number of pixels added increases, for example, from 2×2 binning to 4×4 binning and to binning 8×8, the readout time can be shortened. Since the image obtained by the readout in the exposure detection drive is used to determine switching of the radiation emission energy, the resolution does not need to be considered. Thus, the time needed for the readout may be shortened by significantly decreasing the resolution to 32×32 binning, for example. Alternatively, the number of pixels 112 to be read out may be limited. For example, in order to read out signals only from some of the rows of the pixels, reading out from the other rows may be skipped.

After the signal processing unit 352 determines the timing of the sampling-and-holding SH2, the exposure detection operation is shifted to the energy subtraction drive. Thus, the binning settings, etc. are changed to those of the energy subtraction drive.

Figure 8A:
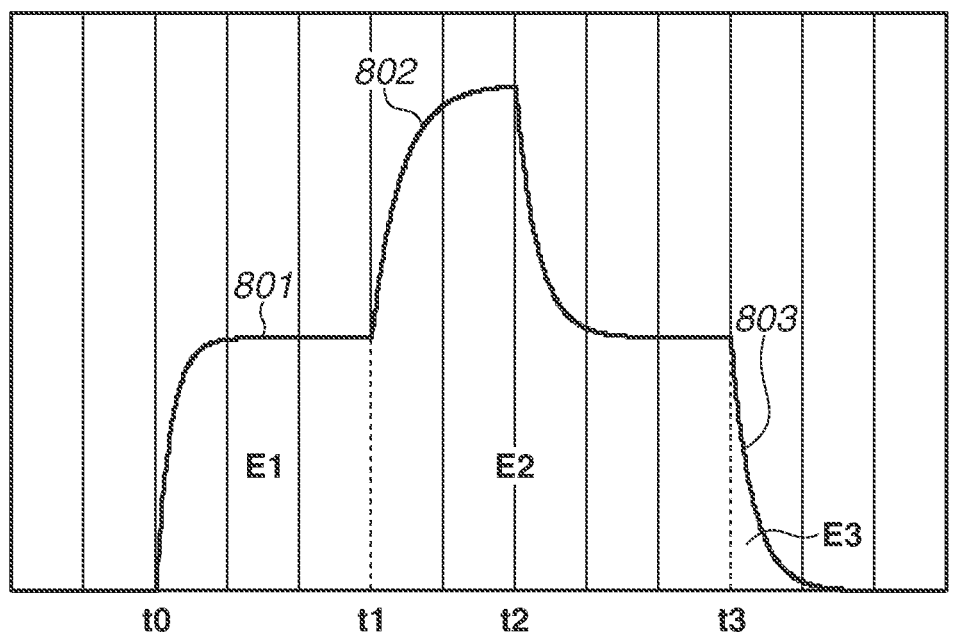
FIG. 8A illustrates an example of emitted radiation and an example of charges held by a charge accumulation unit.
Figure 8B:
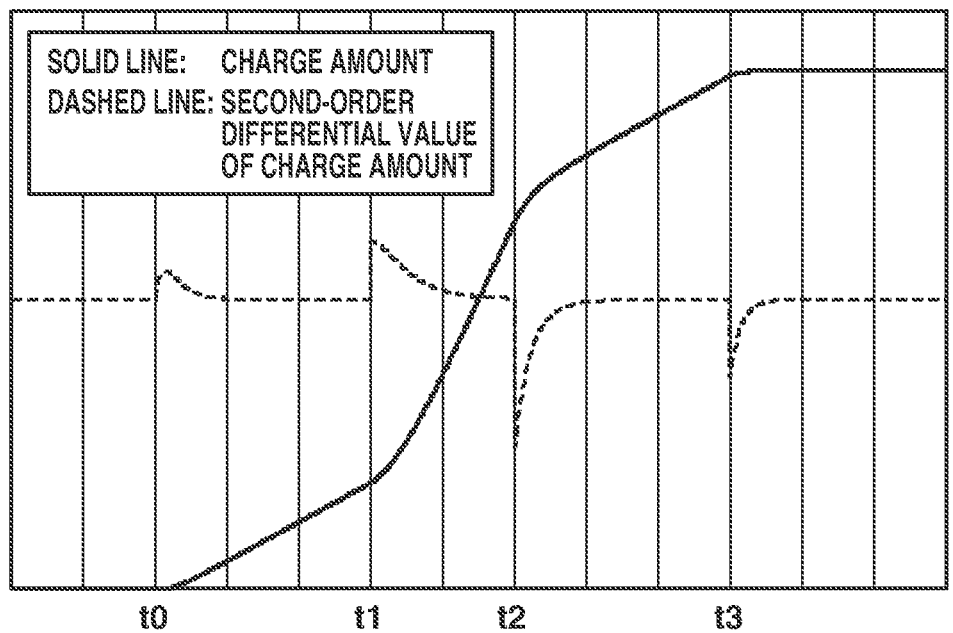
FIG. 8B illustrates an example of emitted radiation and an example of charges held by a charge accumulation unit.

FIGS. 8A and 8B illustrate an example of a method in which the signal processing unit 352 determines the timings of the sampling-and-holdings from the change amount of the signal output from the AD converter 190. FIG. 8A illustrates an example of the temporal change of the radiation energy emitted from the radiation source 400. In FIG. 8B, a solid line represents the temporal change in (integral value of) the signal based on the charge amount held by the charge accumulation unit 211 when the plurality of pixels 112 receives the radiation energy illustrated in FIG. 8A, and a dashed line represents a second-order differential value serving as the differential value of the signal. In FIG. 8A, the exposure of a low energy radiation is started at t0, the exposure of a high energy radiation is started at t1, the high energy radiation starts to fall at t2, and the low energy radiation starts to fall at t3. The integral value (the solid line) and the second-order differential value significantly change at timings t0 to t3 in FIG. 8B, in response to t0 to t3 in FIG. 8A. Here, descriptions have been provided using an example in which an integral value and a differential value (a second-order differential value) are used as the information about the temporal change in (waveform of) the radiation energy. However, any values that represent the temporal change may be used. More preferably, a second-order differential value can be applicable.

Figure 9:
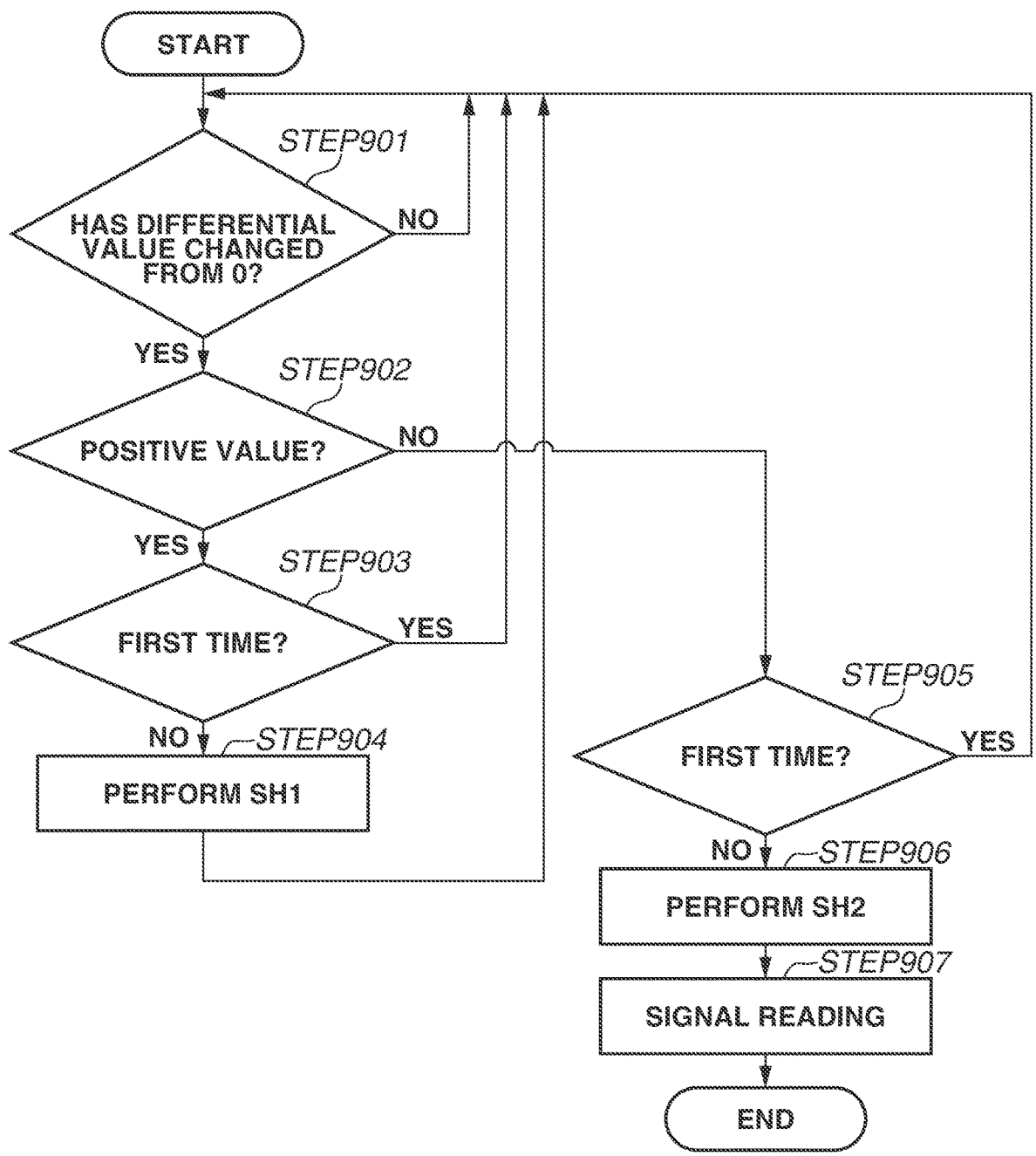
FIG. 9 is a flowchart illustrating an energy subtraction imaging operation according to the present invention.

FIG. 9 exemplifies a flowchart illustrating an operation for one frame when, in response to receiving radiation illustrated in FIGS. 8A and 8B, energy subtraction imaging is performed. Upon the start of the imaging, the detection unit 190 detects change in the charge amount held by the charge accumulation unit 211. If the second-order differential value of the charge amount is adopted, significant change is observed as illustrated in FIG. 8B. In the case of the waveform illustrated in FIG. 8A, the differential value is approximately 0 before the change. Thus, whether or not the differential value has changed from 0 is determined in STEP 901. In STEP 901, if the detection unit 190 detects change in the differential value (YES), in STEP 902, whether or not the differential value is a positive value is determined. If the detection unit 190 does not detect change in the differential value in STEP 901 (NO), STEP 901 is repeated until change in the differential value is detected. In STEP 902, if it is determined that the differential value is a positive value (YES), in STEP 903, the detection unit 190 determines whether the differential value is a first-time positive value. Thus, the detection unit 190 determines whether the timing is timing t0 representing the start of the low energy radiation exposure or timing t1 representing the start of the high energy radiation exposure. In STEP 902, if the detection unit 190 determines that the differential value is a negative value (NO), the processing proceeds to STEP 905, which will be described in detail below. In STEP 903, if the detection unit 190 determines that the differential value is the first-time positive value (YES), the processing returns to STEP 901. If the detection unit 190 determines that the differential value is not a first-time positive value (second-time positive value) (NO), in STEP 904, the detection unit 190 provides a notification to the control unit 130, and the control unit 130 performs the sampling-and-holding SH1.

Thereafter, the detection unit 190 repeats STEP 901 until the detection unit 190 detects the next change in the differential value. If the detection unit 190 detects change in STEP 901 and, in STEP 902, determines that the differential value is a negative value (NO), in STEP 905, the detection unit 190 determines whether the differential value is a first-time negative value. Thus, whether it is a falling edge of a high energy radiation or a falling edge of a low energy radiation is determined. If, in STEP 905, it is determined that it is a first time (YES in STEP 905), the processing returns to STEP 901. In STEP 905, if it is determined that it is not a first time (second time) (NO), in STEP 906, a notification is provided to the control unit 130, and the control unit 130 performs the sampling-and-holding SH2. Next, in STEP 907, read out of a signal is performed. The sampling-and-holding SH3 may uniquely be determined at a predetermined time after the sampling-and-holding SH2 in STEP 907. In this way, the energy subtraction imaging in one frame is completed.

As described above, a sampling-and-holding can be performed at an appropriate timing by acquiring information about the temporal change in (waveform of) the energy of the emitted radiation from change in the charge amount of the charge accumulation unit 211.

In the above description, a mode in which three types of images whose energies are different from each other has been described. However, the present invention is not limited to this mode. For example, four types of images whose energies are different from each other may be acquired by increasing the number of sampling-and-holdings. Alternatively, two types of images whose energies are different from each other may be acquired, by decreasing the number of sampling-and-holdings. Alternatively, two types of images whose energies are different from each other may be acquired from three types of images whose energies are different from each other.

In above examples, the waveform of the tube voltage of the radiation source 400 is intentionally adjusted to obtain a plurality of images whose energies are different from each other, and new radiation images are formed based on the plurality of images. Alternatively, radiation having a wide energy band (wavelength band) may be emitted from the radiation source 400, and the energy of the radiation may be changed by switching of a plurality of filters.

Figure 10:
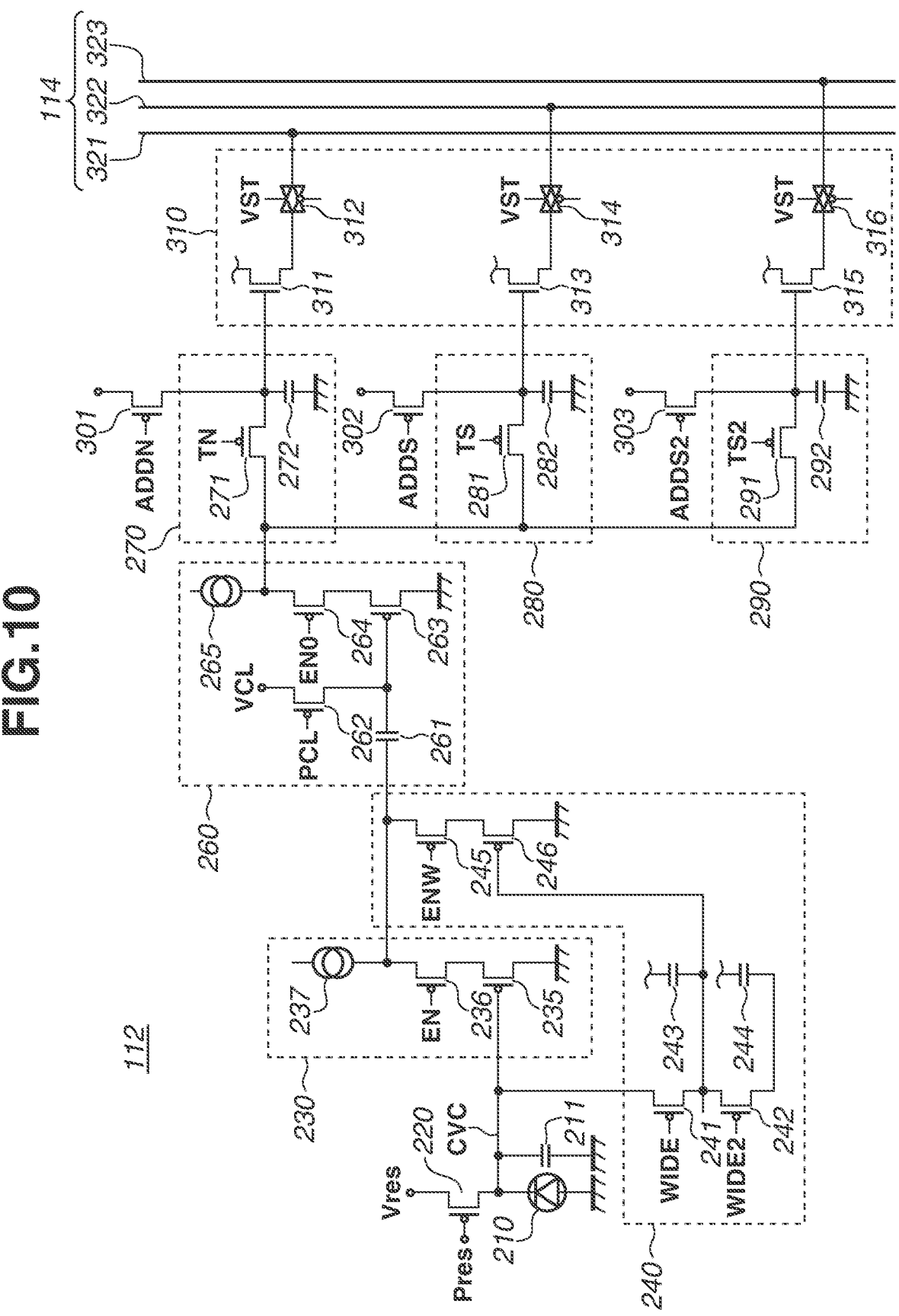
FIG. 10 illustrates a configuration example of a single pixel according to a second exemplary embodiment of the present invention.

FIG. 10 illustrates a configuration of a radiation imaging apparatus 1 according to a second exemplary embodiment of the present invention. The second exemplary embodiment differs from the first exemplary embodiment in that a sample-and-hold circuit 290, an output circuit, and a column signal line are added to the pixel configuration in FIG. 3 so that signal output is made to be three systems. What is not described in the second exemplary embodiment may be the same as in the first exemplary embodiment. In the second exemplary embodiment, a sample-and-hold circuit 290 is further provided separately from the sample-and-hold circuit 270 and the sample-and-hold circuit 280. The output circuit 310 further includes a MOS transistor 315 and a row selection switch 316. The MOS transistor 315 forms a source follower circuit with a current source (not illustrated) connected to a column signal line 323. The sample-and-hold circuit 290 may include a switch 291 and a capacitor 292. The switch 291 is set to on by the row selection circuit 120 activating the sample-and-hold signal TS2. The radiation signal that is output from the clamp circuit 260 is written in the capacitor 292 via the switch 291 by the sample-and-hold signal TS2 being activated.

The signal that is output from the sample-and-hold circuit 290 is made to be a dedicated signal for obtaining the information about the temporal change in (waveform of) the radiation energy, and the control unit 130 drives independently of the energy subtraction drive as illustrated in FIG. 11. In this way, the signal processing unit 352 can obtain detailed information about the temporal change in (waveform of) the radiation energy. At this time, the obtaining of signals from the sample-and-hold circuit 290 is performed at high speed through the above method, and the first signal 805 and the second signal 806 for image generation are read out at certain intervals by, for example, reading out alternately the signals 805 and 806 for each column. Since the reading out of the dedicated signal for obtaining the information about the temporal change in (waveform of) the radiation energy is performed in parallel with the reading out of the first signal 805 and the second signal 806, the time needed for the reading out of the first signal 805 and the second signal 806 is extended. However, while the time needed for the reading out of the first signal 805 and the second signal 806 is on the order of milliseconds (ms), the high-speed reading out is performed on the order of μs. Thus, the image generation and the frame rate are little affected. By arranging a dedicated signal output system for obtaining the information about the temporal change in (waveform of) the radiation energy, the signal processing unit 352 can detect the completion of the emission of the radiation 803 having the energy E3. This enables the determining of the timing of the last sampling-and-holding SH3 based on the detection of the completion of the exposure of the radiation 803 having the last energy E3. This also enables the determining of the timing at which the reset level (0) is sampled and held by the sample-and-hold circuit 270 and the timing at which the third signal 807 is read out.

For the determination of a timing in the present invention, a setting value of the timing previously set may be held and a timing based on the information about the temporal change in (waveform of) the radiation energy may be compared with the setting value previously set, for example. In a case where a comparison result includes a divergence, an inspector may be notified of the presence of divergence, or the setting value that has been set from data corresponding to several frames may be corrected.

The present invention is not limited to the above exemplary embodiments. Various changes and modifications may be made without departing from the spirit and scope of the present invention. Thus, the following claims have been attached to the description, to make the scope of the present invention public.

According to the present invention, there is provided a technique which is advantageous in reducing the variation in time from when the emission of radiation is started to when a signal is sampled and held.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus comprising:
a pixel array including a plurality of pixels; and
a readout circuit configured to read out a signal from the pixel array,
each of the plurality of pixels including:
a conversion element configured to convert a radiation into an electrical signal; and
a sample-and-hold circuit configured to perform sampling-and-holding a plurality of times on a signal from the conversion element in response to the radiation,
wherein the radiation imaging apparatus further comprises:
a processing unit configured to perform processing of determining timings of the plurality of times of the sampling-and-holdings based on information about temporal change in radiation energy of the radiation obtained based on a signal read out by the readout circuit, and
a control unit configured to perform control so that the plurality of times of sampling-and-holdings is performed by the sample-and-hold circuit at the timings determined by the processing unit.

2. The radiation imaging apparatus according to claim 1, wherein the control unit determines the timings of the plurality of times of sampling-and-holdings so that radiation images whose energies are different from each other are obtained.

3. The radiation imaging apparatus according to claim 1, further comprising a reset unit configured to reset the conversion element,
wherein, in each of the plurality of pixels, the reset unit does not reset the conversion element in a period between a first sampling-and holding of the plurality of times of sampling-and-holdings and a last sampling-and holding of the plurality of times of sampling-and-holdings.

4. The radiation imaging apparatus according to claim 3, wherein the control unit controls the plurality of pixels so that a period between a start of emission of a radiation and an end of a sampling-and-holding is constant.

5. The radiation imaging apparatus according to claim 4, wherein the control unit controls the plurality of pixels so that, in a plurality of frames, the period between the start of emission of the radiation and the end of the sampling-and-holding is constant.

6. The radiation imaging apparatus according to claim 5, wherein the control unit controls the readout circuit and the sample-and-hold circuit so that the information about the temporal change in the radiation energy is obtained based on a signal read out by the readout circuit.

7. The radiation imaging apparatus according to claim 6, wherein the processing unit further performs processing of detecting the start of emission of the radiation based on a signal read out by the readout circuit, and
wherein the control unit controls the readout circuit so that a repetition of the reading out by the readout circuit in detecting the start of emission of the radiation is performed more quickly than a repletion of the reading out by the readout circuit in obtaining the radiation images having the plurality of energies.

8. The radiation imaging apparatus according to claim 7, wherein the control unit performs control so that the reset unit resets the conversion element before the start of emission of the radiation is detected.

9. The radiation imaging apparatus according to claim 3, wherein the processing unit determines the timings of the plurality of times of sampling-and-holdings based on a temporal change amount of a signal read out by the readout circuit.

10. The radiation imaging apparatus according to claim 3, wherein each of the plurality of pixels includes, as the sample-and-hold circuit, another sample-and-hold circuit configured to obtain the information about the temporal change in the radiation energy, separately from the sample-and-hold circuit configured to obtain the radiation images having the plurality of energies.

11. The radiation imaging apparatus according to claim 10, wherein the processing unit determines a timing of the last sampling-and-holding of the plurality of times of sampling-and-holdings at a timing corresponding to completion of emission of the radiation, based on a signal from the another sample-and-hold circuit.

12. The radiation imaging apparatus according to claim 11, wherein the processing unit determines, based on a signal from the another sample-and-hold circuit, a timing of the reset after the last sampling-and-holding and a timing of sampling-and-holding of a reset level when the reset is performed, at the timing corresponding to the completion of emission of the radiation.

13. A method for controlling a radiation imaging apparatus including a pixel array including a plurality of pixels and a readout circuit configured to read out a signal from the pixel array, each of the plurality of pixels including a conversion element configured to convert a radiation into an electrical signal and a sample-and-hold circuit configured to perform a sampling-and-holding a plurality of times on a signal from the conversion element in response to the radiation, the control method comprising:
causing the sample-and-hold circuit to perform the plurality of times of sampling-and-holdings at timings determined based on information about temporal change in radiation energy of the radiation obtained based on a signal read out by the readout circuit.

* * * * *